(12) United States Patent
Morawietz et al.

(10) Patent No.: US 6,265,623 B1
(45) Date of Patent: Jul. 24, 2001

(54) PROCESS FOR THE REDUCTIVE CLEAVAGE OF LINEAR AND CYCLIC ACETALS ESPECIALLY FORMALS

(75) Inventors: Marcus Morawietz, Hanau; Thomas Haas, Frankfurt; Olaf Burkhardt, Alzenau; Rudolf Vanheertum, Kahl, all of (DE)

(73) Assignee: Perstorp Specialty Chemicals AB, Perstorp (SE)

( * ) Notice: Subject to any disclaimer, the term of this patent is extended or adjusted under 35 U.S.C. 154(b) by 0 days.

(21) Appl. No.: 09/384,058

(22) Filed: Aug. 26, 1999

(30) Foreign Application Priority Data

Sep. 4, 1998 (DE) ................................ 198 40 276

(51) Int. Cl.$^7$ .......................... C07C 29/132; C07C 29/10
(52) U.S. Cl. ............................. 568/853; 568/854
(58) Field of Search ...................... 568/853, 854

(56) References Cited

FOREIGN PATENT DOCUMENTS

| 42 20 939 A1 | 1/1994 | (DE) . |
|---|---|---|
| 44 14 274 A1 | 10/1995 | (DE) . |
| WO 97/01523 | 1/1997 | (WO) . |

OTHER PUBLICATIONS

Derwent WPI, "Alcohol Production by Cataytic Aldehyde . . . Impregnated With a Noble Metal", Abstract DE 44124274 A, (1994).

Derwent WPI, "2–Aryl–Ethanol Compounds . . .Useful as Aroma of Fragrance", Abstract DE 4220939 A, (1995).

*Primary Examiner*—Peter O'Sullivan
(74) *Attorney, Agent, or Firm*—Pillsbury Winthrop LLP

(57) ABSTRACT

The reductive cleavage of linear and cyclic acetals, especially formals, in an aqueous medium containing a formate takes place by hydrogenation with hydrogen in the presence of a heterogeneous hydrogenation catalyst at a pH value of less than 7 at a temperature of over 200° C. The catalyst-poisoning effect of the formate is overcome at over 200° to 300° C., especially from over 200° to 280° C., so that, in a suspension procedure, the weight ratio of metal having hydrogenating activity to acetal is less than 0.1.

10 Claims, No Drawings

PROCESS FOR THE REDUCTIVE CLEAVAGE OF LINEAR AND CYCLIC ACETALS ESPECIALLY FORMALS

CROSS-REFERENCE TO RELATED APPLICATION

This application relates to German Application DE 198 40 276.7, filed Sep. 4, 1998, which disclosure is incorporated herein by reference.

FIELD OF THE INVENTION

The invention relates to a process for the reductive cleavage of linear and cyclic acetals, especially formals. The invention is directed especially towards the hydrogenolytic cleavage of cyclic formals in an aqueous medium in the presence of a formate, especially an ammonium, alkali metal or alkaline earth metal formate, wherein 1,3-diols and methanol are formed.

BACKGROUND OF THE INVENTION

Even though the hydrolysis of formals and other acetals is one of the fundamental reactions of organic chemistry, problems can still occur where the equilibrium position is one-sided, as is the case, for example, with cyclic acetals having a 1,3-dioxo structure, owing to inadequate selectivity and side reactions, including thermal decomposition.

Linear and cyclic acetals, especially formals, are formed as undesired secondary products in the large-scale preparation of polyhydric alcohols, such as pentaerythritol, trimethylol-propane, trimethylol-ethane, neopentyl glycol and oligomers of those alcohols, which includes an aldol addition and a Cannizzaro reaction. In the Cannizzaro reaction, which is carried out in the presence of an alkali metal, alkaline earth metal or ammonium hydroxide, the corresponding formate is formed. The formate is present in the various stages of working up of the polyols in varying amounts.

WO 97/01523 describes a process for the cleavage, by hydrogenation, of cyclic formals, such as are formed as secondary products in the case of an aldol addition with a subsequent Cannizzaro reaction to prepare polyhydric alcohols, such as pentaerythritol and trimethylolpropane, to the underlying diols and methanol. The cleavage takes place in the aqueous phase at a pH of from 1 to 6 in the presence of a heterogeneous metal catalyst at from 100° to 200° C. under a hydrogen atmosphere. As is shown by Example 1 of that document, a previously acidified aqueous reaction mixture from the preparation of di-trimethylolpropane (di-TMP), which also contains sodium formate in addition to the cyclic formals di-TMP and tri-TMP to be cleaved and unidentified compounds, is hydrogenolyzed in the presence of Ru on activated carbon at 67 bar $H_2$ and 130° C.

As was discovered by the inventors of the present Application when re-working WO 97/01523, the hydrogenolysis under the mentioned pressure and temperature conditions can only be carried out successfully if it is based on a very high weight ratio of catalytically active metal to cyclic formal. This ratio is 0.91 in the Example mentioned. The formate contained in the reaction mixture evidently acts as a catalyst poison. However, such a high relative amount of catalyst used renders the process uneconomical. Therefore, the object of the invention is to improve the above-mentioned process.

SUMMARY OF THE INVENTION

In the process in question, the acetal cleavage is to take place as quantitatively as possible but, at the same time, the formation of unsaturated and color-giving compounds is to be avoided.

The object is achieved by a process for the reductive cleavage of linear and cyclic acetals, especially formals, in an aqueous medium containing a formate, in the presence of a heterogeneous hydrogenation catalyst and hydrogen, at a pH value of less than 7, a pressure of from 0.1 to 30 MPa and a temperature of over 100° C., which process is characterized in that the reaction is carried out at a temperature of over 200° up to 300° C., wherein, in the case of a suspension procedure, the weight ratio of metal having hydrogenating activity to acetal is less than 0.1.

It has been found that the catalyst-poisoning effect of the formates can, surprisingly, be eliminated merely by raising the temperature. In this manner, it is possible to carry out the hydrogenolytic cleavage of linear and cyclic acetals with a high degree of selectivity for the 1,3-diol underlying the acetal, using an amount of catalyst that is substantially lower as compared with the prior art. In that process it is possible, in the presence of a formate, to cleave not only the acetals per se, but also linear and cyclic formals, such as may be contained as secondary products in reaction mixtures from the combined aldol addition and Cannizzaro reaction.

Studies show that the negative influence of the formate on the hydrogenation catalyst diminishes almost abruptly only at or above a temperature of 160° C., and the cleavage even of cyclic formals to the polyhydric alcohol and methanol proceeds sufficiently rapidly and completely. In general, the temperature is from above 200° to 300° C. and the reaction takes place especially preferably at from above 200° to 280° C.

Suprisingly, it is also possible to feed to the cleavage according to the invention an aqueous solution, containing an acetal, which is very weakly acid (pH>6) or even neutral at room temperature. It is, therefore, not absolutely necessary to adjust the pH to an acid value, as was necessary in the prior-known process. A pH value of the solution of 7 (at 20° C.) leads to a value of less than 7 at the reaction temperature used. The presence of an acid catalyst in the process according to the invention does not have an adverse effect but, rather, speeds up the reaction slightly. The acids may be protic inorganic or organic acids, or acid fixed catalysts whose $H_o$ value of the Hammett acidity function is less than +2, preferably less than −3 (Tanabe et al. in "Surface Science and Catalysis" Vol. 51 (1989),5). Mineral acids are less preferred, because they must be neutralized after the reaction and the salts must be separated from the reaction mixture and disposed of. Where an acid is used, preference is given to lower carboxylic acids, especially formic acid. A pH value of, for example, from 1 to 6 is suitable. Where acid fixed catalysts are used, for example those from the group of natural and synthetic silicate-like substances, such as mordenite, montmorillonite and acid zeolites, and oxides, mixed oxides, cation exchangers, the amount used is determined by the activity of the catalyst at the chosen reaction temperature. Acid fixed catalysts can be used in suspension form or in the form of a fixed bed.

The process according to the invention is carried out in the presence of a conventional hydrogenation catalyst at a pressure in the range of from 0.1 to 30 MPa. The hydrogen partial pressure is advantageously in the range of from 0.5 to 15 MPa, preferably from 1 to 5 MPa and especially from 1 to 3 MPa. Heterogeneous hydrogenation catalysts are preferred because they allow the catalyst to be separated from the reaction mixture in a simple manner—separation of a suspension catalyst by filtration, or arrangement of the catalyst as a fixed bed, for example in the case of a trickling bed or bubble column procedure.

Conventional hydrogenation catalysts contain as the active component a noble metal from the group Ru, Rh, Pd and Pt, or a transition metal from the group Cu, Cr, Co, Ni, Fe, including especially Raney catalysts and chromite catalysts; bimetallic catalysts of a transition metal and a noble metal may also be used, although they are not preferred because they have a limited useful life. The use of a hydrogenation catalyst containing one or more transition metals is advantageous only if the catalyst is sufficiently stable to acid under the reaction conditions.

Preferred hydrogenation catalysts for the process according to the invention are noble metal catalysts in metallic form, such as so-called blacks of Ru, Rh and, especially, Pd and Pt, or in a form bonded to a support. Suitable support materials for Ru, Rh, Pd and Pt are activated carbon, aluminium oxide, $SiO_2$, $TiO_2$ and other metal oxides, as well as silicates. The amount of noble metal in noble metal catalysts bonded to a support is usually in the range of from 0.0001 to 10 wt. %, preferably in the range of from 0.01 to 5 wt. %. The optimum amount of noble metal catalyst to be used, which depends on the activity of the catalyst, the reaction temperature and the $H_2$ pressure, will be determined by the person skilled in the art by means of preliminary experiments. It is also possible to use a catalyst containing both acid functions and functions having hydrogenating activity, for example a zeolite partially laden with a noble metal. An advantage of the process according to the invention is that, when a suspension hydrogenation catalyst is used, the weight ratio of the metal having hydrogenating activity to the acetal to be cleaved is less than 0.1 and preferably less than 0.01. When a fixed bed hydrogenation catalyst is used, it is possible, while maintaining the temperature according to the invention, to work with LHSV values (liquid hourly space velocity) of, for example, equal to or greater than $1^{-1}$, which are customary in the art and permit a good space-time yield.

By means of the process according to the invention for acetal cleavage, acetals of mono- or polyhydric alcohols, especially polyhydric primary alcohols, or mixtures containing such acetals are obtainable. The acetals are based preferably on lower aliphatic or aromatic aldehydes, especially on formaldehyde; acetals of formaldehyde (=formals) are often present in linear or cyclic form simultaneously. It is important that the acetal or formal is sufficiently soluble in the aqueous, salt-containing solution under the reaction conditions. The acetals and formals can contain further functional groups, provided that those groups are not hydrogenated or hydrolyzed under the hydrogenation conditions according to the invention.

According to the invention, especially aliphatic acetals may be cleaved hydrogenolytically, preferably formals from the group of the 1,3-dioxanes and 1,3-dioxolanes, which are based on diols, triols, tetrols and polyols and polyol ethers. Examples of diols are ethylene glycol, propylene glycol, propane-1,3-diol, butane-1,4-diol, hexane-1,6-diol, neopentyl glycol; examples of triols are glycerol, trimethylolethane (TME), trimethylolpropane (TMP), hexane-1,2,6-triol; an example of a tetrol is pentaerythritol, and examples of polyols are di- and tri-TMP and di- and tri-pentaerythritol.

The acetal or formal cleavage according to the invention is carried out in an aqueous medium containing a formate, especially an alkali metal, ammonium or alkaline earth metal formate. If required, the solution to be cleaved may also contain mono- or polyhydric alcohols and/or, additionally, other solvents which are stable to acid and hydrogenation, such as an aprotic dipolar solvent. The use of a purely aqueous or aqueous-alcoholic solution is, however, preferred. The acetals and the water are advantageously used in a weight ratio in the range of from 10:1 to 1:100, preferably in the range of from 2:1 to 1:20. It is especially preferred to use reaction mixtures containing formals and a formate, as are formed in an aldol addition with a subsequent Cannizzaro reaction or within the context of their working up.

The process can be carried out continuously or discontinuously. In the case of a continuous procedure and the use of a suspension hydrogenation catalyst, the solution to be treated, containing an acetal and a formate, can be fed continuously to a centrifugal reactor containing the suspension catalyst, and a corresponding portion can be expelled via a filter. The process is especially preferably carried out continuously using a fixed bed hydrogenation catalyst. Working up of the reaction mixture once the reaction is complete—the optimum reaction time will be determined by the person skilled in the art by means of preliminary experiments—is carried out in the manner known to the person skilled in the art using conventional steps, such as filtration, crystallization, distillation, etc. The composition of the reaction mixture or of individual fractions is analyzed by means of GC or HPLC chromatography. Polyols and polyol ethers are preferably silylated with hexamethyldisilazane/DMF prior to analysis and are subsequently analyzed by means of GC chromatography.

Advantages of the process according to the invention are the high degree of selectivity in the formation of the alcohols from the acetals, the substantially smaller amount of catalyst used, and the increased space-time yield. The process is simple to carry out, and the use of an acid catalyst is optional.

DETAILED DESCRIPTION OF THE PREFERRED EMBODIMENTS

The invention is explained further in comparison with the prior art by means of the Examples and Comparative Examples which follow.

Comparative Example 1 (CE 1)

Test to react pentaerythritolmonoformal to produce pentaerythritol in the presence of sodium formate, analogously to the process described in WO 97/01523.

100 g of pentaerythritolmonoformal, 23 g of sodium formate (2 wt. % of the reaction solution), 1000 g of 0.1% aqueous $H_3PO_4$ solution and 10.1 g of hydrogenation catalyst (3% Ru on activated carbon) were placed in a 2 liter autoclave. A hydrogen pressure of 4 MPa was applied at room temperature, and the reaction mixture was then heated to 150° C., during which the pressure rises to approximately 6 MPa. The mixture was stirred at that temperature for 180 minutes. After cooling, the autoclave was emptied, the catalyst was filtered off, and a representative sample was taken. The water was removed completely using a rotary evaporator, a colorless liquid was obtained, and the residue was subjected to quantitative analysis by means of GC. The cleavage of the formal was totally inadequate.

The analytical data are to be found in the Table.

Comparative Example 2 (CE 2)

Test to react pentaerythritolmonoformal to produce pentaerythritol in the presence of calcium formate, analogously to the process described in WO 97/01523.

The reaction was carried out analogously to Comparative Example 1, but 23 g of calcium formate were used instead of sodium formate. In this case too, the conversion of the formal was totally inadequate.

The analytical data are to be found in the Table.

EXAMPLE 1 (E 1)

Reaction according to the invention of pentaerythritol-monoformal to produce pentaerythritol in the presence of calcium formate.

25 g of pentaerythritolmonoformal, 500 g of water and 25 g of calcium formate were added together; the mixture was adjusted to pH 5 using a small amount of formic acid and, after the addition of 3 g of hydrogenation catalyst (5% Ru on activated carbon) the mixture was placed in a 1 liter autoclave. A hydrogen pressure of 2 MPa was applied at room temperature, and the reaction mixture was then heated to 280° C. (pressure rise to approximately 10 MPa). The mixture was stirred at that temperature for 60 minutes. After cooling, the autoclave was emptied, the catalyst was filtered off, and a representative sample was taken. The water was removed completely using a rotary evaporator, and a colorless solid was obtained. The residue was subjected to quantitative analysis by means of GC. The reaction, i.e. the cleavage of the formal to pentaerythritol, was virtually quantitative.

The analytical data are to be found in the Table.

EXAMPLE 2 (E 2)

Reaction of a solution containing pentaerythritolformals, pentaerythritol and higher polyols from an industrial process for the preparation of pentaerythritol from acetalaldehyde, formaldehyde and calcium hydroxide.

500 g of a solution having the following composition:

| | |
|---|---|
| 4 wt. % | linear and cyclic pentaerythritolformals |
| 18 wt. % | pentaerythritol |
| 3 wt. % | di-/tri-pentaerythritol |
| 8 wt. % | calcium formate |
| 67 wt. % | water | and 3 g of hydrogenation catalyst (5% Ru on activated carbon) were adjusted to pH 5–6 using a small amount of formic acid and placed in a 1 liter autoclave. A hydrogen pressure of 2 MPa was applied at room temperature; the reaction mixture was then heated to 250° C. (pressure rise to approximately 8.5 MPa). The mixture was stirred at that temperature for 120 minutes. After cooling, the autoclave was emptied at 40° C., the catalyst was filtered off, and a representative sample was taken. The water was removed completely using a rotary evaporator, and a colorless solid was obtained; the residue was subjected to quantitative analysis by means of GC. The formals were definitely cleaved quantitatively, and pentaerythritol was formed with a high degree of selectivity.

The analytical data are to be found in the Table.

EXAMPLE 3 (E 3)

Example 2 was repeated, but the reaction was carried out at 280° C. over a period of 60 minutes instead of 250° C./120 minutes. In this case too, a comparably good result was achieved.

The analytical data are to be found in the Table.

Comparative Example 3 (CE 3)

Reaction of a mixture of pentaerythritol, pentaerythritol-formals and higher polyols to a mixture of pentaerythritol and higher polyols in the presence of a small amount of calcium formate.

500 g of a solution having the following composition:

| | |
|---|---|
| 4 wt. % | linear and cyclic pentaerythritolformals |
| 29 wt. % | pentaerythritol |
| 4 wt. % | di-/tri-pentaerythritol |
| 0.5 wt. % | calcium formate |
| 62.5 wt. % | water | and 3 g of hydrogenation catalyst (5% Ru on activated carbon) were adjusted to pH 5–6 using a small amount of formic acid and placed in a 1 liter autoclave. A hydrogen pressure of 2 MPa was applied at room temperature, and the reaction mixture was then heated to 140° C. The mixture was stirred at that temperature for 180 minutes. After cooling, the autoclave was emptied at 40° C., the catalyst was filtered off, and a representative sample was taken. The water was removed completely using a rotary evaporator, a colorless solid was obtained, and the residue was subjected to quantitative analysis by means of GC. The reaction was very incomplete.

The analytical data are to be found in the Table.

Comparative Example 4 (CE 4)

500 g of solution having the composition of Comparative Example 3 were treated hydrogenolytically with the amount of catalyst indicated in CE 3 at 150° C. over a period of 180 minutes (instead of 140° C./180 minutes). Only a slight conversion of formal could be detected.

The analytical data are to be found in the Table.

EXAMPLE 4 (E 4)

500 g of solution having the composition of Comparative Example 3 were treated hydrogenolytically with the amount of catalyst indicated in CE 3 according to the invention at 180° C. over a period of 120 minutes. A very high conversion of formal and a very high degree of selectivity were obtained.

The analytical data are to be found in the Table.

The principal difference and effect of the process according to the invention (E 4) in comparison with the prior-known process (CE 3 and CE 4) becomes especially clear when the yield of pentaerythritol, which can be determined from the conversion and the selectivity (see Table), is considered: CE 3 (140° C.) approximately 1%, CE 4 (150° C.) approximately 10%, and E 4 approximately 86%.

EXAMPLE 5 (E 5)

500 g of solution having the composition of Comparative Example 3 were treated hydrogenolytically with the amount of catalyst indicated in CE 3 according to the invention at 200° C. over a period of 120 minutes, but without previously adjusting the solution to pH 5–6 using formic acid. A very high conversion of formal and a very high degree of selectivity were obtained.

The analytical data are to be found in the Table.

TABLE

| No. | Conversion (%, based on formals used) | Pentaerythritol selectivity (%, based on converted formals) |
|---|---|---|
| CE 1 | <10 | <11 |
| CE 2 | 36 | 11 |
| E 1 | >99 | 98 |
| E 2 | 95 | 91 |
| E 3 | 98 | 90 |
| CE 3 | <5 | 25 |
| CE 4 | 35 | 31 |
| E 4 | 93 | 94 |
| E 5 | 90 | 89 |

What is claimed is:

1. A process for the reductive cleavage of linear and cyclic acetals, in an aqueous medium containing a formate, in the presence of a heterogeneous hydrogenation catalyst and hydrogen, at a pH value of less than 7 and a pressure of from 0.1 to 30 Mpa, comprising:
    carrying out the reaction at a temperature of above 200° to 300° C., wherein, in the case of a suspension procedure, the weight ratio of metal having hydrogenating activity to acetal is less than 0.1.

2. The process according to claim 1, comprising:
    carrying out the reaction at a temperature of from above 200° to 280° C.

3. The process according to claim 1, comprising:
    feeding to the reductive cleavage a reaction mixture from an aldol addition and a Cannizzaro reaction, containing at least one member selected from the group consisting of cyclic formals and linear formals as secondary products and sodium, calcium or ammonium formate as coupling product.

4. The process according to claim 1, comprising:
    using as the catalyst a supported catalyst based on an activated carbon or an oxidic support with one or more metal(s), having hydrogenating activity, from the group Ru, Rh, Pd, Pt, Cu, Cr, Fe, Co and Ni.

5. The process according to claim 4, comprising:
    using as the catalyst at least one member selected from the group consisting of Ru on active carbon and Pd on activated carbon.

6. The process according to claim 1, comprising:
    adjusting the pH value of the aqueous solution to be fed to the cleavage by hydrogenation to a pH of from 4 to 7.

7. The process according to claim 6, comprising:
    adjusting the pH value to a pH of from above 6 to 7.

8. The process according to claim 1, comprising:
    carrying out the cleavage by hydrogenation using a fixed bed catalyst in a trickling bed or bubble column procedure.

9. The process according to claim 1, comprising:
    carrying out the cleavage at an $H_2$ partial pressure of from 1 to 5 MPa, especially from 1 to 3 MPa.

10. The process according to claim 1, wherein the linear and cyclic acetals comprise formals.

* * * * *